United States Patent [19]

Drewlow

[11] Patent Number: Plant 6,308

[45] Date of Patent: Sep. 27, 1988

[54] IMPATIENS PLANT NAMED SUNBURST

[75] Inventor: Lyndon W. Drewlow, Ashtabula, Ohio

[73] Assignee: Mikkelsens, Inc., Ashtabula, Ohio

[21] Appl. No.: 916,567

[22] Filed: Oct. 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Sunburst, having deep orange and near white bicolored flowers; large broad green leaves with purple midrib; compact, self-branching, mounded growth habit, and having two flowers per axil and floriferous habit.

2 Drawing Sheets

The present invention relates to a new and distinctive cultivar of Impatiens plant, botanically known as Impatiens, and referred to by the cultivar name Sunburst. Sunburst was developed by me through controlled breeding by crossing Mikkelsen Seedling No. 84-1031-1 (seed parent) with Mikkelsen Seedling No. 84-1578-15 (pollen parent). Asexual reproduction of the progeny of the stated cross by terminal or stem cuttings performed in Ashtabula, Ohio has shown that unique features of this new impatiens are stabilized and are reproduced true to type in successive propagations.

The following characteristics in combination distinguish the new impatiens from both its parent varieties and other cultivated impatiens of this type known and used in the floriculture industry. In certain instances the characteristics are compared with similar characteristics of other cultivars. Of the cultivars referred to, Astro is disclosed in U.S. Plant Pat. No. 4,691, and Sunregal, Sunglow, Sundazzle, and Twilight are disclosed in pending applications.

1. Sunburst has a distinct dark orange and almost white bicolor which is similar in pattern to Sunglow, Sundazzle and Sunregal, cultivars with which the present cultivar is being compared. Twilight is only slightly bicolored, and Astro is bicolored only on the upper petal.

2. Sunburst has a medium reddish main stem which is similar to Sunglow and Astro. Sundazzle has a lighter green stem with red tint, and Twilight and Sunregal have stems with a deep purple color.

3. Sunburst has a larger flower than Sunglow, is similar in size to Sundazzle, and is smaller than the flowers of Sunregal, Twilight and Astro.

4 Sunburst is similar in plant size and mounded growth form to Sundazzle. Sunglow is larger in size. Sunregal is slightly larger with a more upright habit of growth. Astro and Twilight are taller and more open in growth habit.

5. Sunburst has a small area of cream variegation near the midrib of mature leaves, while Astro, Sunglow and Twilight are heavily variegated. Sunregal and Sundazzle have no variegation in the leaves.

6. Sunburst has large broad leaves similar in size to Sundazzle, Twilight and Astro. The leaves of Sunregal and Sunglow are smaller.

7. Sunburst has yellow-green leaves similar in color to Sundazzle. Sunregal has shiny green leaves. Astro has more purple in the green, and Twilight and Sunglow are a dull dark green in leaf color.

8. Sunburst has two flowers per leaf axil which is similar to Sunregal, Sunglow and Sundazzle. Twilight and Astro have only one flower per leaf axil .

9. Sunburst is compact, highly self-branched, and vigorous with a mounded growth habit making it suitable for 4" pots, hanging baskets, and bedding plant use.

10. Flowering of Sunburst is 6 to 10 days earlier than Astro and Twilight, 2 to 5 days earlier than Sunglow and similar to Sundazzle and Sunregal.

In the accompanying colored photographs, sheet 1 is a perspective view of Sunburst, showing the colors as true as it is reasonably possible to obtain in a colored reproduction of this type. Sheet 2 is an enlarged color photograph showing in more detail the bicolor flowers.

The following is a detailed description of my new impatiens cultivar based on plants produced under commercial practices in Ashtabula, Ohio under both greenhouse and outdoor conditions. Photographs were taken of greenhouse grown plants in early June. Color references are made to the Royal Horticultural Society Colour Chart except where general terms of ordinary dictionary significance are used.

Parentage: A controlled cross between Mikkelsen Seedling No. 84-1031-1 and Mikkelsen Seedling No. 84-1578-15.

Propagation:

(A) *Type cutting.*—Stem 15 mm long will develop to 4 to 5 cm long in 18 to 21 days.

(B) *Time to root.*—8 to 10 days at 23° C. summer, and 10 to 12 days at 20° C. winter.

(C) *Rooting habit.*—Heavy, fibrous.

Plant description:

(A) *Form.*—Symmetrically mounded, compact, self-branching, red stemmed, vigorous growing flowering herb.

(B) *Habit of growth.*—Self-branching, compact, vigorous, mounded, continuous flowering once flowering has started.

(C) *Foliage description.*—Yellow-green leaves with reddish purple midrib, narrow cream variegation at midrib near base of leaf on mature leaves in full light. (1) Size: Mature foliage 11 to 12 cm long and 3.0 to 3.5 cm wide at the widest point. (2) Shape: Lanceolate with acuminate apex and acute base. (3) Texture: Slightly rugose upper surface, glabrous underside. (4) Margin: Entire with fine cilia. (5) Color: Young foliage top side 146A. Under side: 187B. Mature foliage top side 147A, variegated with 153D. Under side: 183B. (6) Venation: Pinnate with reddish midribs.

Flowering description:

(A) *Flowering habits.*—Flowers continuously from leaf whorl in progressively orderly manner taking 5 to 7 days from bud to bloom. Each leaf axil has two flower buds, and the secondary ones do not open until all primary flowers in an axil have opened. Before the secondary flowers finish opening the primary flowers on the whorl above start to open. Flowers can last 2 to 3 weeks.

(B) *Natural flowering season.*—Indeterminant and continuous. Quantity of flowers increases with increasing levels of light.

(C) *Flower buds.*—Ellipsoidal, flowers perfect, pinkish green spur 3.0 cm long on mature buds with throat behind ovary and originating from the major sepal.

(D) *Flowers borne.*—On individual short 4 cm pinkish red pedicels at maturity from a whorl of 6 leaves; flowering progressively around the whorl with all primary flowers in a whorl opening before the secondary ones start to open.

(E) *Quantity of flowers.*—Very floriferous due to the two flowers per leaf axil; flowering development is continuous so that tight buds and mature flowers are present at the same time.

(F) *Petals.*—(1) Shape: Heart shaped; upper and two lower petals are similar in size. (2) Color: Top side in summer when opening, 34A and 49C streaked with 49A; fading to 34A with greater amounts of 49C and lesser amounts of 49A; under side 41C and 49C. (3) Number of petals: Five (5) in number. (4) Size of flowers: 4.5 to 5 cm in diameter.

(G) *Reproductive organs.*—(1) Stamens: Five (5) in number. (a) Anther shape: Hooded, color cream. (b) Pollen color: Cream. (2) Pistels: (a) Stigma: Five (5) in number, segmented column shaped, color purplish. (b) Style color: Purplish. (c) Ovaries: Five (5) in number, celled, 5 mm until fertilized, color green with slight purple tint.

Disease resistance: No significant disease or insect problems noted to date.

SUMMARY OF IMPORTANT CHARACTERISTICS OF NEW CULTIVAR

1. Distinct deep orange and almost white bicolor on mature dark foliage with only slight variegation provides a pleasant contrast.

2. Ability to flower and set buds under low light and 70° F. temperatures without leaf drop or fading of flowers.

3. Many breaks for good propagation.

I claim:

1. A new and distinct Impatiens plant named Sunburst, as described and illustrated, and particularly characterized by its deep orange and near white bicolored flowers; large broad green leaves with purple midrib; compact, self-branching, mounded growth habit, and by its two flowers per axil and floriferous habit.

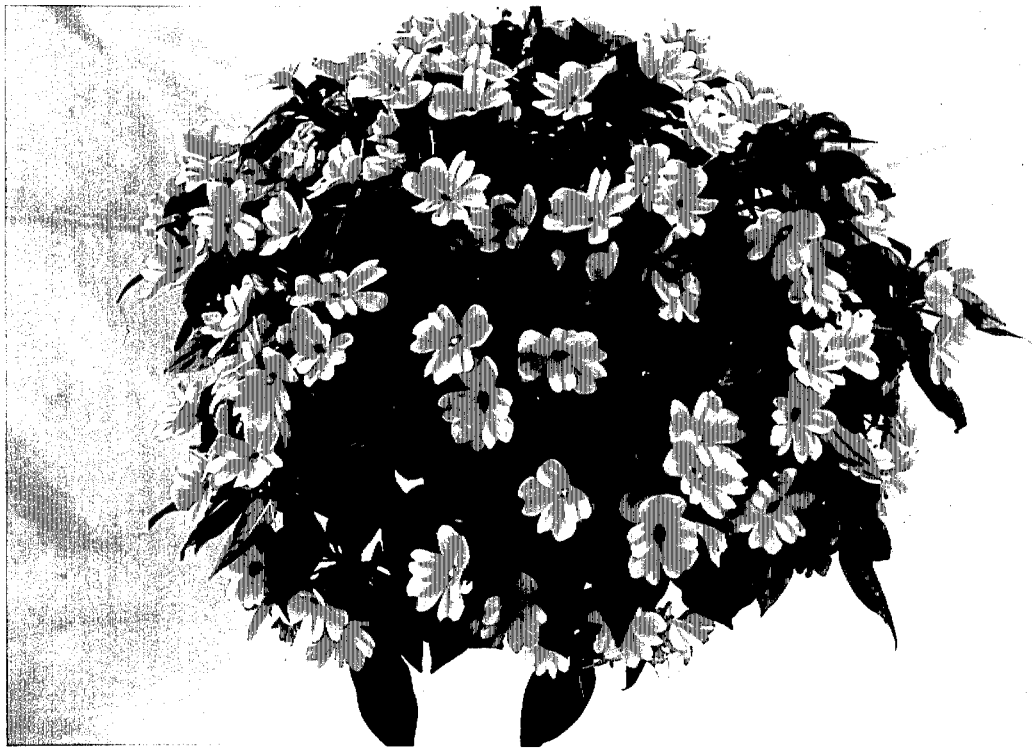

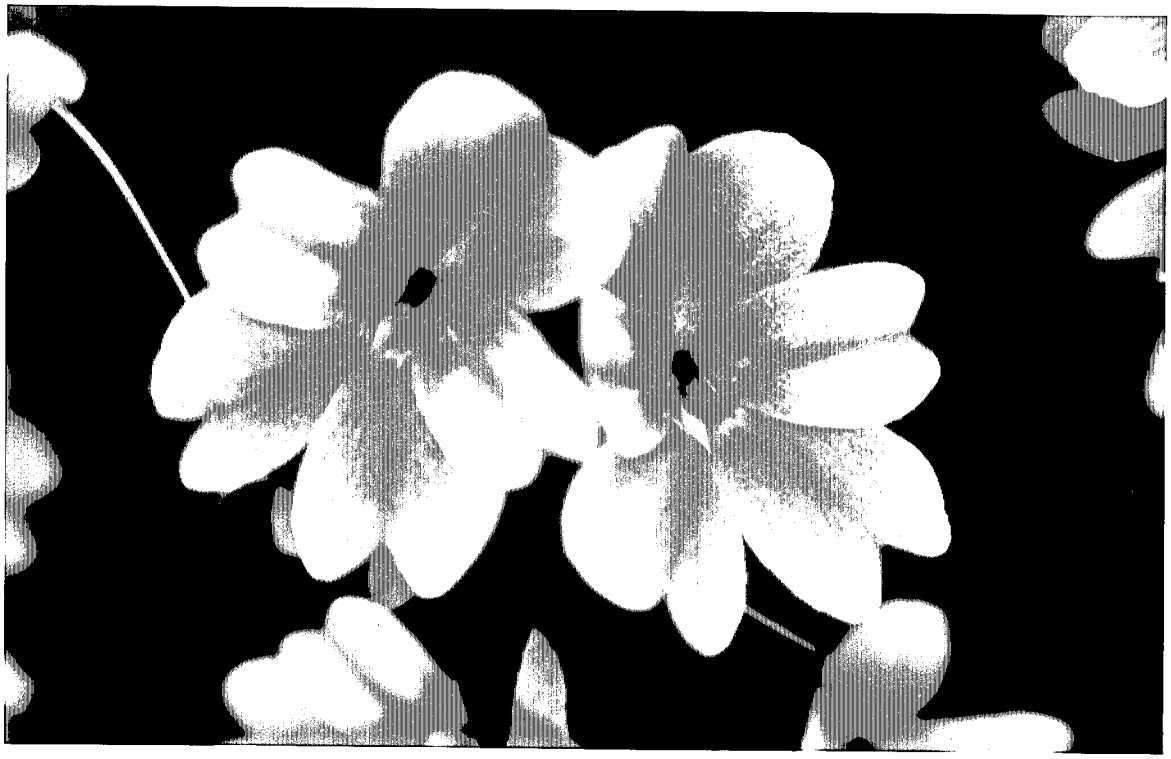

* * * * *